US008519348B2

(12) United States Patent
Topfer et al.

(10) Patent No.: US 8,519,348 B2
(45) Date of Patent: Aug. 27, 2013

(54) IMAGE QUALITY MONITOR FOR DIGITAL RADIOGRAPHY SYSTEM

(75) Inventors: Karin Topfer, Rochester, NY (US); Richard T. Scott, Hilton, NY (US); Timothy J. Wojcik, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 429 days.

(21) Appl. No.: 12/643,276

(22) Filed: Dec. 21, 2009

(65) Prior Publication Data

US 2011/0057802 A1    Mar. 10, 2011

Related U.S. Application Data

(60) Provisional application No. 61/240,373, filed on Sep. 8, 2009.

(51) Int. Cl.
G01T 1/17    (2006.01)

(52) U.S. Cl.
USPC ..................... 250/370.11; 382/132

(58) Field of Classification Search
USPC ..................... 382/132; 250/370.11
See application file for complete search history.

(56) References Cited

U.S. PATENT DOCUMENTS

| | | | |
|---|---|---|---|
| 5,657,400 A | 8/1997 | Granfors et al. | 382/254 |
| 6,919,568 B2 | 7/2005 | Odogba et al. | 250/370.09 |
| 7,026,608 B2 | 4/2006 | Hirai | 250/252.1 |
| 7,394,925 B2 | 7/2008 | Hayashida | 382/132 |
| 2004/0239782 A1 | 12/2004 | Equitz et al. | 348/246 |
| 2006/0204065 A1 | 9/2006 | Hsieh et al. | 382/128 |
| 2007/0165934 A1 | 7/2007 | Maac et al. | 382/132 |
| 2008/0192899 A1* | 8/2008 | Kump et al. | 378/207 |
| 2009/0212226 A1* | 8/2009 | Britton et al. | 250/370.07 |

OTHER PUBLICATIONS

R Padgett and C J Kotre "Assessment of the effects of pixel loss on image quality in direct digital radiography", Phys. Med. Biol. 49 pp. 977-986, 2004.
James A. Seibert, John M. Boone, and Karen K. Lindfors "Flat-field correction technique for digital detectors," Proc. SPIE vol. 3336, 1998, pp. 348-354.

* cited by examiner

Primary Examiner — Constantine Hannaher

(57) ABSTRACT

A system for monitoring the state of calibration of a digital x-ray detector having a solid state sensor with a plurality of pixels, a scintillating screen and at least one embedded microprocessor, the system having means for capturing a digital image and a computer operable during normal diagnostic use of the detector, in cooperation with at least one embedded microprocessor, for performing pixelwise computations on the image and calculating a misregistration metric indicative of movement of the solid state sensor relative to the scintillating screen. A defect metric indicative of abnormal properties of pixels in the solid state sensor is calculated. It is then determined whether one or both of the misregistration metric and the defect metric exceeds a respective, preselected threshold value. The user of the system is alerted to conduct a calibration of the detector when either one or both of the respective threshold values have been exceeded.

21 Claims, 12 Drawing Sheets

IMAGE QUALITY MONITOR FOR DIGITAL RADIOGRAPHY SYSTEM

CROSS-REFERENCE TO RELATED APPLICATIONS

Priority is claimed to U.S. Provisional Application Ser. No. 61/240,373, titled IMAGE QUALITY MONITOR FOR DIGITAL RADIOGRAPHY SYSTEM, by Topfer et al, filed Sep. 8, 2009.

FIELD OF THE INVENTION

This invention generally relates to digital radiography (DR) imaging and more particularly relates to a method for monitoring DR detector performance in order to identify the need for recalibration.

BACKGROUND OF THE INVENTION

Digital Radiography (DR) detectors directly transform received exposure energy to digital image data. These detectors commonly contain an array of light sensitive picture elements, or pixels, arranged in a matrix of rows and columns and a scintillator, consisting of a material, such as gadolinium oxisulfide, $Gd_2O_2S$:Tb (GOS) or cesium iodide, that absorbs x-rays incident thereon and converts the x-ray energy to visible light photons. In some configurations, the scintillator is in direct contact with the light sensitive array. The array of light sensitive elements can be any type of solid state sensor, such as a flat panel detector, a charge-coupled device, or CMOS detector. The light sensitive material converts the incident light into electrical charge which is stored in the internal capacitance of each pixel. The magnitude of the stored electrical charge is related to the intensity of the excited light, which is, in turn, related to the intensity of the incident x-rays. The radiation image exposures captured on radiation-sensitive layers are converted, pixel by pixel, to electronic image data which is then stored in memory circuitry for subsequent read-out and display on suitable electronic image display devices.

Much like video sensors and other types of two-dimensional solid state image detectors, DR detectors include several thousands of picture elements, or pixels. Inevitably, some number of pixels are found to be defective. Provided that this number is relatively small, the defective pixels can be tolerated and their impact on image quality can be minimized, as described by R Padgett and C J Kotre in "Assessment of the effects of pixel loss on image quality in direct digital radiography", Phys. Med. Biol. 49 977-986, 2004. Frequently, specifications exist for the maximum number of allowable defects and the largest size of allowable defect clusters to maintain the required image quality.

Compensation techniques such as defect mapping and corrective image processing allow the use of DR detectors having defective pixels, provided that such pixels can be detected and proper steps taken for correcting the image. Defect mapping for image sensors is generally taught, for example, in U.S. Pat. No. 5,657,400 by Granfors et al. entitled "Automatic Identification and Correction of Bad Pixels in a Large Area Solid State X-ray Detector" and in U.S. Pat. No. 6,747,697 by Lin et al. entitled "Method and Apparatus for Digital Image Defect Correction and Noise Filtering".

Defect mapping and correction procedures are commonly coupled with gain and offset calibration and correction procedures, which compensate for pixel-to-pixel variations in sensitivity and dark current. The most basic calibration and correction algorithms generally include two steps as taught by James A. Seibert, John M. Boone, and Karen K. Lindfors in "Flat-field correction technique for digital detectors," Proc. SPIE Vol. 3336, 1998, p. 348-354. First, the dark signal of the detector (that is, the signal in the absence of any X-ray exposure) is obtained. Pixel by pixel variations in the dark signal of the detector are characterized to form a dark or offset map containing the dark variations. The offset map is then subtracted from the X-ray exposure in a process termed dark or offset correction. Secondly, variations in the sensitivity of the pixels are characterized. This is done by capturing one or more flat field exposures, which are then offset-corrected. The resulting image is the gain map. In the gain correction step, the offset-corrected X-ray exposure is divided by the gain map. Ideally, this two-step procedure compensates for any fixed pattern noise introduced by the detector.

Defect identification methods often explore anomalies in the gain and offset maps produced during calibration, for example by identifying pixels with gain and offset values that differ significantly from their surroundings, and by setting upper and lower thresholds for allowable values in gain and offset maps, to update the defect maps for a given detector as described in the previously cited Granfors et al. '400 disclosure and in U.S. Pat. No. 6,919,568 to Odogba et al. entitled "Method and Apparatus for Identifying Composite Defective Pixel Map". Thus, periodic recalibration can help to manage defective pixels with conventional DR detectors and can help to produce corrected images with few, if any, visible defective pixels.

Conventional DR detectors generally accumulate few additional defective pixels over time and require infrequent recalibration. These detectors are often permanently mounted on a wall stand, in an examination table or some type of gantry or other type of adjustable framework that provides a secure mechanical mount for positioning the detector behind the patient and at a proper disposition with respect to the x-ray source. In addition to this mechanical support, the conventional DR system provides a "tethered" arrangement, with cabling for power and data to the DR detector. Even some tethered detectors may be somewhat portable; however, such devices typically have thick, rigid covers protecting the sensor and scintillating screen from any outside forces.

Advances in miniaturization, packaging, and data communications now make it possible to provide a more portable DR detector that may be as thin as a conventional film X-ray cassette. Wireless operation, moreover, eliminates the need for data cabling to the DR detector, making it easier to position the detector relative to the patient or other imaged subject. The use of an on-board battery eliminates the need for external power connection, enabling the DR detector to be positioned and handled in a manner similar to that of a film cassette or Computed Radiography (CR) cassette.

With the advent of more portable DR detector devices comes considerable promise for more flexible and adaptable imaging systems that can help to improve the efficiency and quality of patient care. However, there are some disadvantages related to the portability of such a device. Unlike film and CR cassettes, a portable DR detector contains a considerable amount of complex miniaturized circuitry. Rough handling of such a device, for example, can lead to some abrasion damage across the sensor surface, thus increasing the likelihood of defects and requiring additional calibration cycles in order to update the defect map. Moreover, with increasingly more compact packaging, environmental factors such as temperature variation can also cause the detector to need more frequent calibration. In addition, normal and rough handling of the detector can result in subtle motion of the scintillating screen relative to the sensor panel, resulting in localized changes in gain. These gain changes, which can be corrected by performing a gain calibration, have the appearance of misregistration artifacts.

Because of the factors discussed above, the required intervals between calibration procedures, needed for maintaining suitable image quality, are less predictable for fully portable detectors. One solution would be simply to require more frequent calibration for these units. Calibration could thus be required, for example, after a certain number of images were taken. However, this type of arbitrary interval negatively impacts productivity. Calibration procedures require radiology staff time and attention and each calibration reduces the overall utilization time of the DR detector.

Clearly, there is a need to monitor the calibration state of the detector' during regular clinical operation and to alert the user when calibration is needed. Various methods have been proposed for performing such monitoring. One solution, such as that proposed in U.S. Pat. No. 7,026,608 to Hirai, entitled "Gain Correction of Image Signal and Calibration for Gain Correction", analyzes clinical images themselves to determine if recalibration is needed. If the threshold for recalibration is exceeded, the user is prompted to capture a flat field exposure after obtaining the clinical image. The ratio of the existing gain map to the newly acquired flat field is used to correct the image. This procedure may detect the need for calibration, but effectively disrupts operator workflow and increases access time for obtaining the current fully corrected clinical image. This disruption and time loss may be unacceptable in many clinical environments. In critical situations, such as in the emergency room or intensive care unit, for example, valuable time would be lost.

Another method for monitoring the calibration state of the detector during clinical operation is that described in U.S. Patent Application Publication Number 2007/0165934 entitled "Device and Method for Correcting Defects in X-Ray Images", to Maac et al. In the method described by Maac et al., clinical images that have been fully corrected for gain, for offset, and for previously identified defects are routinely analyzed for new defects, and a defect candidate map is formed containing the new defects. Over time, the new defects from the defect candidate map are added to the permanent defect map only if they occur in a sufficient number of images. This method, although it may prove successful enough for a non-portable, mounted DR detector, falls short of what is needed for fully portable digital X-ray detectors. Such methods fail to distinguish between misregistration artifacts, which can be eliminated by performing a gain calibration, and truly defective pixels that need to be added to the defect map. For portable detectors, the method described in the Maac '5934 disclosure, despite the safeguards provided by adding defects to the candidate defect map first, would lead to the identification of pixels that do not belong in the permanent defect map. As a result, the detector would eventually exceed the threshold for the number of allowable defects and would have to be taken out of operation.

In summary, while there are some indications that conventional pixel defect detection methods may perform well enough when used within more permanent DR detector installations, these same methods do not appear to successfully address particular requirements of the portable DR detector. It has been found, for example, that conventional methods fail to distinguish between correctable misregistration problems that can be characteristic of portable devices, and truly defective pixels. This shortcoming limits the effectiveness of conventional approaches and makes these known solutions less desirable for the more rigorous requirements of the portable DR detector. There is, thus, a need for a method for monitoring performance of a portable DR detector in order to identify the need for recalibration, wherein this method is particularly suited to the needs of portable DR detectors.

SUMMARY OF THE INVENTION

It is an object of the present invention to advance the art of diagnostic imaging, particularly as related to the use of portable digital radiography detectors. With this object in mind, the present invention provides a system for monitoring the state of calibration of a digital x-ray detector, the detector comprising a solid state sensor with a plurality of pixels, a scintillating screen and at least one embedded microprocessor, the system comprising: means for capturing a digital image; and a computer operable during normal diagnostic use of the detector, in cooperation with at least one embedded microprocessor, for performing pixelwise computations on the image and calculating a misregistration metric indicative of movement of the solid state sensor relative to the scintillating screen; calculating a defect metric indicative of abnormal properties of pixels in the solid state sensor; determining whether one or both of the misregistration metric and the defect metric exceeds a respective, preselected threshold value; and alerting a user of the system to conduct a calibration of the detector when either one or both of the respective threshold values have been exceeded.

It is a feature of the present invention that it distinguishes defective pixels from misregistered pixels for a portable DR detector.

It is an advantage of the present invention that it tracks both correctable and non-correctable pixel-based imaging anomalies for a portable DR detector.

These objects, features, and advantages are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DETAILED DESCRIPTION OF THE INVENTION

Figure 1:
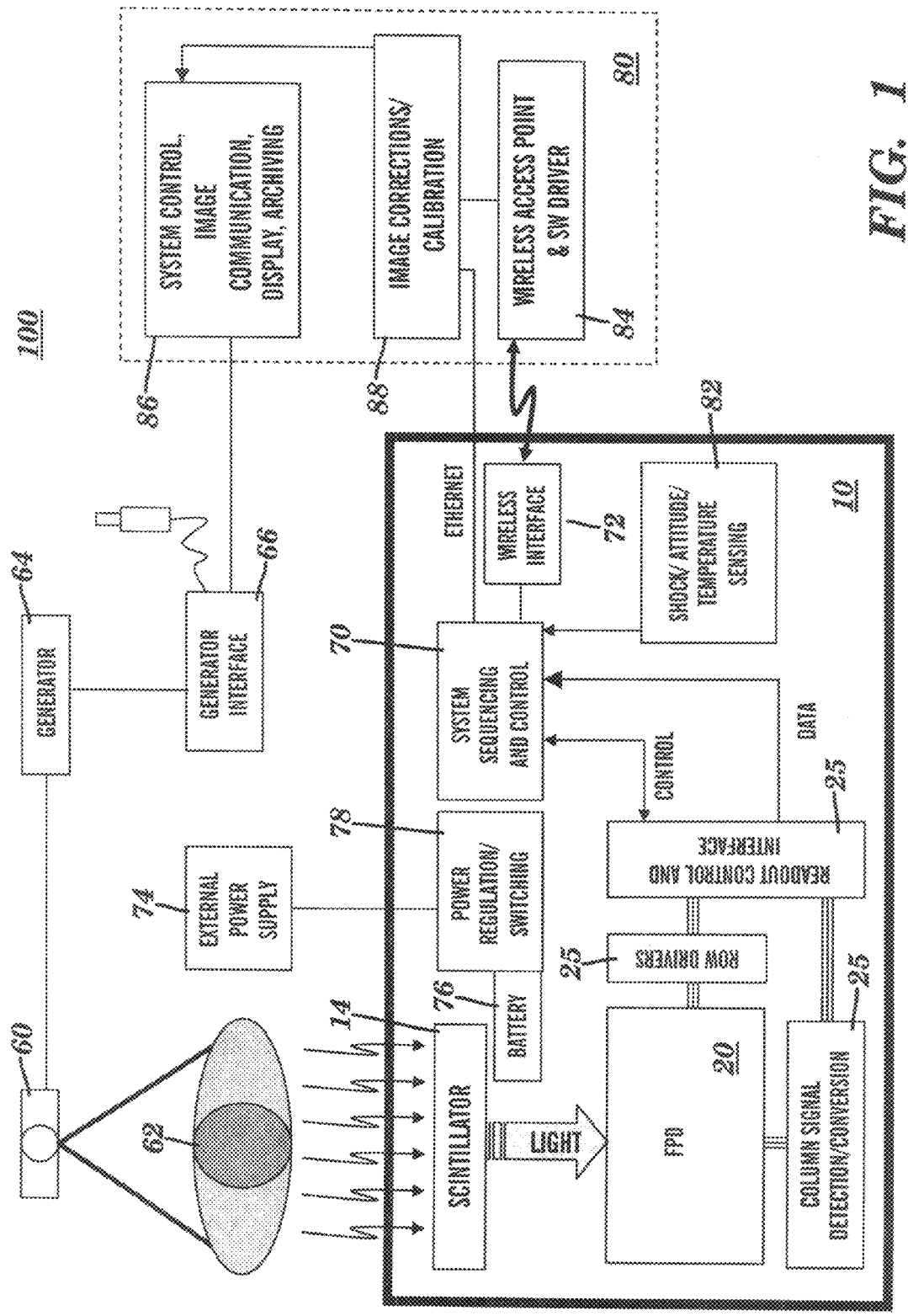
FIG. 1 is a schematic diagram showing the architecture of a radiographic system using a portable DR detector.

The following is a detailed description of the preferred embodiments of the invention, reference being made to the drawings in which the same reference numerals identify the same elements of structure in each of the several figures.

The term "set", as used herein, refers to a non-empty set, as the concept of a collection of elements or members of a set is widely understood in elementary mathematics. The term "subset" as used herein refers to a non-empty subset of a set having one or more members. For a set S, a subset may comprise the complete set S (improper subset) or may have fewer members than the complete set S (proper subset).

A DR detector system and particular requirements for a portable. DR detector are described with reference to FIG. 1. The schematic diagram of FIG. 1 shows, at a high level, the basic architecture of a radiographic system 100 that uses a portable DR detector 10. An x-ray source 60, with a supporting generator 64 and a generator interface 66 directs radiation toward a patient or other subject 62 and toward DR detector 10. Components of DR detector 10 include a scintillator screen 14 that responds to the radiation by emitting light to a flat-panel detector (FPD) 20 that is a two-dimensional array of sensing pixels. Row and column readout elements 25, obtain the sensed data under control of commands from a control logic processor 70, such as an embedded microprocessor. Output image data is provided to an external host computer 80 over a data link, such as a wireless interface 72 in the embodiment shown. A cable connection could alternately be supplied for this data link. An external power supply 74 or on-board battery 76 provides source power to a power regulator 78. Optional sensors 82 are provided for shock, temperature, and device orientation. Shock sensor 82 can be used for monitoring mechanical shock to the detector. Shock detection can be used by control logic processor 70 to a system user to conduct a calibration of the detector when a preselected shock threshold value has been exceeded, for example. Temperature detection can operate similarly to signal needed calibration of the detector when a preselected upper or lower temperature threshold value has been exceeded. Either or both, shock and temperature events can lead to loss of calibration of the detector. In the embodiment shown, host computer 80 has a wireless interface 84 or other suitable interface for cabled data connection, for example 100base-T Ethernet, control circuitry 86, and image correction and calibration circuitry 88 for control and processing of image data obtained from DR detector 10. A display screen (not shown) is provided for viewing image data and for reporting information relevant to DR detector 10.

Figure 2:
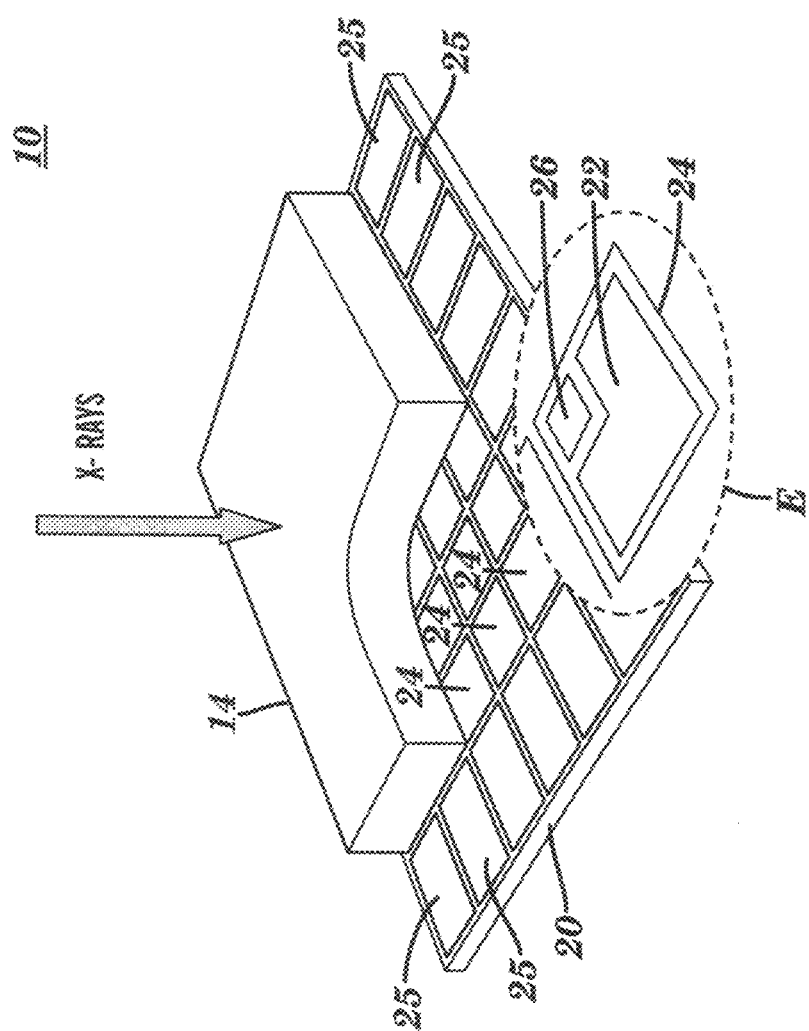
FIG. 2 is a perspective, partial cutaway view showing a portion of a DR detector.

The perspective view of FIG. 2 shows a partial cutaway view of a small edge portion of DR detector 10 of the indirect type. A scintillator screen 14 responds to incident x-ray radiation by generating visible light that is, in turn, detected by a flat panel detector 20. Detector 20 has a two-dimensional array having many thousands of radiation sensitive solid-state sensor pixels 24 that are arranged in a matrix of rows and columns and are connected to readout element 25. Readout element 25 is generally termed an ASIC (Application-Specific Integrated Circuit) or ASIC chip. As shown at enlarged section E, each pixel 24 has one or more photosensors 22, such as a PIN diode or other light-sensitive component, and an associated switch element 26 of some type, such as one or more thin film transistors, or TFTs. To read out image information from the panel, each row of pixels 24 is selected sequentially and the corresponding pixel on each column is connected in its turn to a charge amplifier (not shown). The outputs of the charge amplifiers from each column are then applied to ASIC chips and related circuitry that generate digitized image data that then can be stored and suitably image-processed as needed for subsequent storage and display.

Embodiments of the present invention are implemented in computer and other control logic processor hardware and supporting storage media that are associated with radiographic system 100. This includes control logic functions that are executed by host computer 80 in cooperation with control logic processor 70 (FIG. 1) and, optionally, additional embedded processors, such as microprocessors that are part of DR detector 10. In this context, cooperation between the computer and control logic processor 70 means, for example, that these devices communicate via a wired or wireless protocol. As part of this cooperation, logic control signals can originate at the host as well as at the embedded processors. Some part or all of the computations can be shared, performed on both the host computer and the embedded processors, or may be executed on either of them. Embodiments of the invention may also be embodied in the form of computer program code containing instructions embodied in tangible media, such as various forms of magnetic or optical storage media, hard drives, or any other computer-readable storage medium, wherein, when the encoded instructions are loaded into and executed by a computer or other logic processor, the computer or other processor becomes an apparatus for practicing the invention. The present invention can also be embodied in the form of computer program code, for example, whether stored in a storage medium, loaded into and/or executed by a computer or processor, or transmitted over some transmission medium, such as over electrical wiring or cabling, through fiber optics, or via electromagnetic radiation, wherein, when the computer program code is loaded into and executed by a computer or other type of logic processor, the computer or processor becomes an apparatus for practicing the invention.

Figure 3B:
FIG. 3B is a plan view that shows example misregistration artifacts in an image.
Figure 3A:
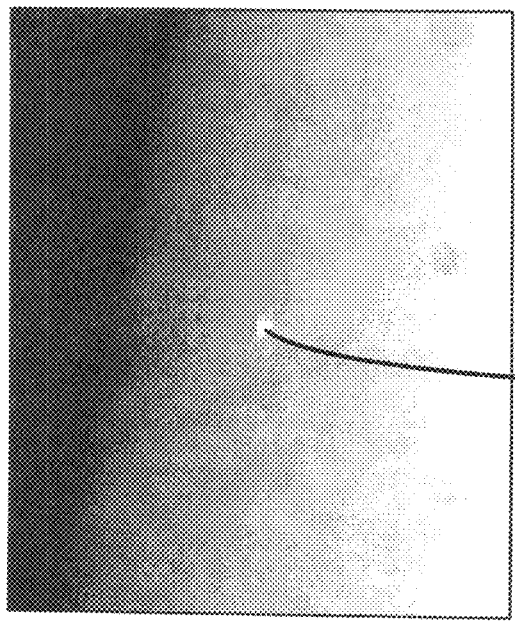
FIG. 3A is a plan view that shows a cluster of defective pixels from a portion of a clinical image.

When implemented on a general-purpose computer, processor, or microprocessor, the computer program code segments configure the computer, processor, or microprocessor to create specific logic circuits. The system and method of the present invention provide pixelwise computation and tracking of pixel performance in a DR x-ray detector in order to monitor the state of calibration of the detector. Unlike conventional DR detector monitoring processes that merely identify defective pixels and maintain a map of defective pixel locations, the system and method of the present invention provides utilities that identify and track the type of defect. The approach of the present invention is thus based on the fact that pixel defects can be of different types. A first type of identified defect may indicate an ongoing intrinsic problem with pixel sensor circuitry that impacts gain and offset values; the locations of first type of defect are often stored in a defect map and can then be compensated for using interpolation and other corrective techniques. FIG. 3A shows an enlarged portion of an image with a defective pixel 30. A second type of defect may indicate a transitory problem that is related to movement and consequent misregistration of a pixel with its corresponding scintillator screen location; this second type of defect can be significantly reduced by periodic recalibration of the DR x-ray detector. FIG. 3B shows an enlarged portion of an image with misregistered pixels 32.

Using methods that distinguish and track both types of pixel-related problems, the method of the present invention provides improved monitoring of the overall calibration state of a portable digital x-ray detector. Advantageously, the method of the present invention performs its monitoring function during normal diagnostic use by analyzing a clinical image or patient image, rather than requiring a separate calibration or target image for pixelwise analysis, as described in the Hirai '608 disclosure noted earlier.

The two types of defects discussed above can be observed in a portable DR environment. Loss of calibration has two different aspects:

(1) Temporary changes in pixel sensitivity. These transitory pixel defects appear to be primarily due to slight shifting of scintillator screen 14 (FIG. 2) relative to the solid state sensor panel indicated as flat-panel detector 20. This shifting can be caused by mechanical shock in detector handling or by temperature changes during operation. This type of misregistration has been found to result in noticeable high frequency, localized gain changes as the locations of these gain variations are no longer in registration with those acquired during the previous calibration. These changes are temporary and can be compensated for in performing a gain calibration.

(2) Pixel defects that result from aging of the detector or more pronounced mechanical stress. These defects include pixels whose offset and gain characteristics drift beyond acceptable tolerances. The pixels themselves can be detected as part of the gain calibration process and added to the current defect map, so that they are fully corrected in subsequently captured X-ray images.

Figure 4:
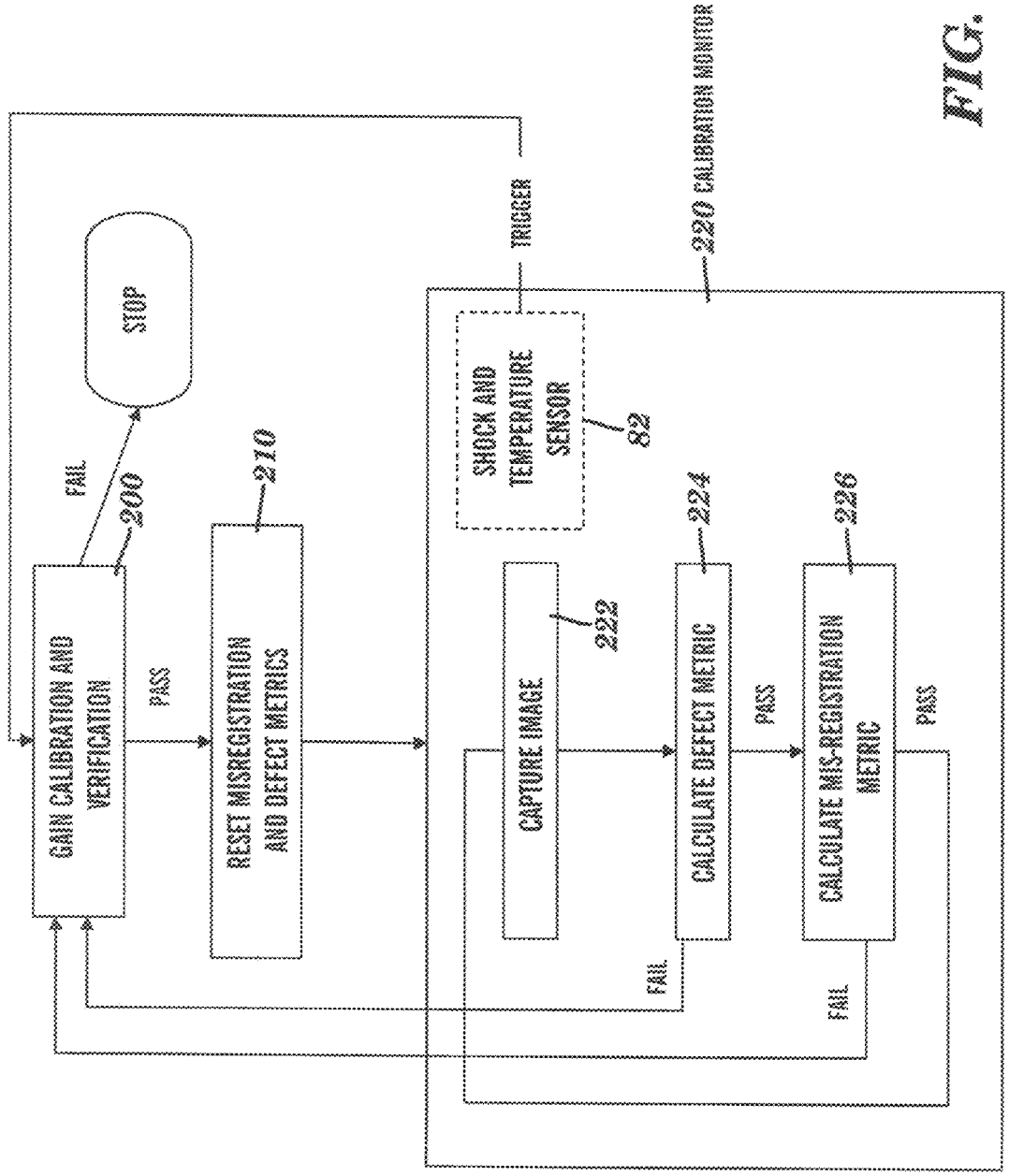
FIG. 4 is a logic flow diagram that shows the function of the calibration monitor of the present invention relative to gain calibration processing.

The overall system of gain calibration and gain calibration monitoring is shown in the logic flow diagram of FIG. 4. A gain calibration monitoring process 220 begins after a gain calibration procedure 200, shown in more detail in FIG. 5, has been performed and the defect and misregistration metrics have been set to zero in step 210.

The calibration monitoring algorithm 220, shown in more detail in FIGS. 6-9, runs regularly during normal imaging following an image capture step 222 and continually performs pixelwise computations on diagnostic images that have been fully corrected with respect to gain, offset, and defects, to identify individual pixels or small clusters of pixels that differ from their surroundings. The algorithm calculates a defect metric in a defect metric calculation step 224 based on a defect pixel count that is indicative of abnormal pixel properties for the flat panel sensor according to aspect (2) defined above. Then, in a misregistration calculation step 226, it calculates a misregistration metric to quantify the loss of calibration according to aspect (1) described above. If either or both the misregistration metric and/or a defect metric exceed a predetermined threshold value, the user is alerted to conduct a gain calibration for the DR detector. The user alert can be by means of a message on an image display screen, a visible indicator on the DR detector itself, or an audible tone, for example. Optionally, the algorithm may correct the identified defective pixels in the current and future images. The predetermined threshold values are empirically derived, based on experience with DR detector performance in clinical environments. A gain calibration can also be triggered by shock and/or temperature sensors 82 (FIG. 1) embedded in the detector if preselected thresholds are exceeded. These thresholds are preferably set such that they only respond to severe deviations from normal handling of the detector, for example if the detector is dropped. In such cases, immediate attention by the operator is warranted without relying on the calibration monitoring algorithm 220. Thus the calibration monitoring algorithm and the shock sensors work together to track both, long-term in small changes to the calibration state of the detector and sudden, severe changes.

Figure 5:
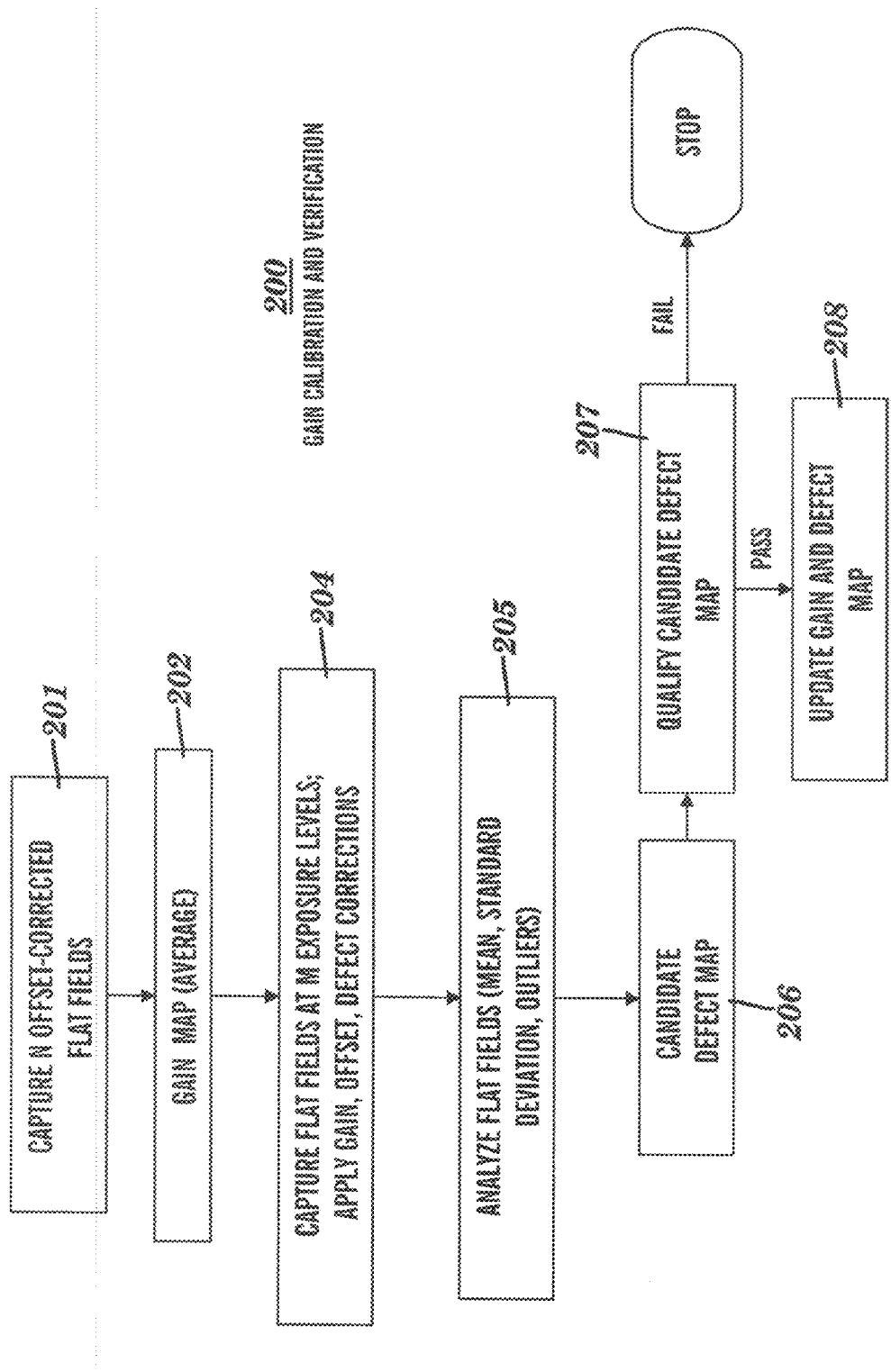
FIG. 5 is a logic flow diagram showing a sequence of steps for gain calibration processing.

The logic flow diagram of FIG. 5 shows basic steps for initial gain calibration procedure 200 and recalibration according to one embodiment. A first capture step 201 obtains a number (N) of offset-corrected flat-field images. An averaging step 202 generates a gain map as a result. A second capture step 204 captures a number of flat-field images at a number (m) of exposure levels and applies gain, offset, and defect corrections. An analysis step 205 then obtains statistical and other data from the flat-field images, such as mean and standard deviation values, and forms a candidate defect map 206 from the identified statistical outliers in the flat field images. This identifies pixels that differ by more than a pre-specified multiple of the standard deviation from the mean as defective pixels. A qualification step 207 follows to check if the total number of defects and the maximum defect size are still within specification limits for the detector, after which defect mapping is updated in an update step 208. Alternately, processing is terminated in the event of failure, due to problems such as detection of excessive defects for this DR detector, low gain signal, or larger than expected gain nonuniformities, for example. Those skilled in the art will recognize that other methods to update defect maps in connection with a gain calibration can be employed, for example direct analysis of the new gain and offset maps, such as is described in the previously cited Granfors et al. '400 disclosure or as described in U.S. Patent Application Publication 2006/0204065 A1 to Hsieh et al., entitled "Method and System for Providing Defective Cell Correction in a Medical imaging Device".

Figure 6:
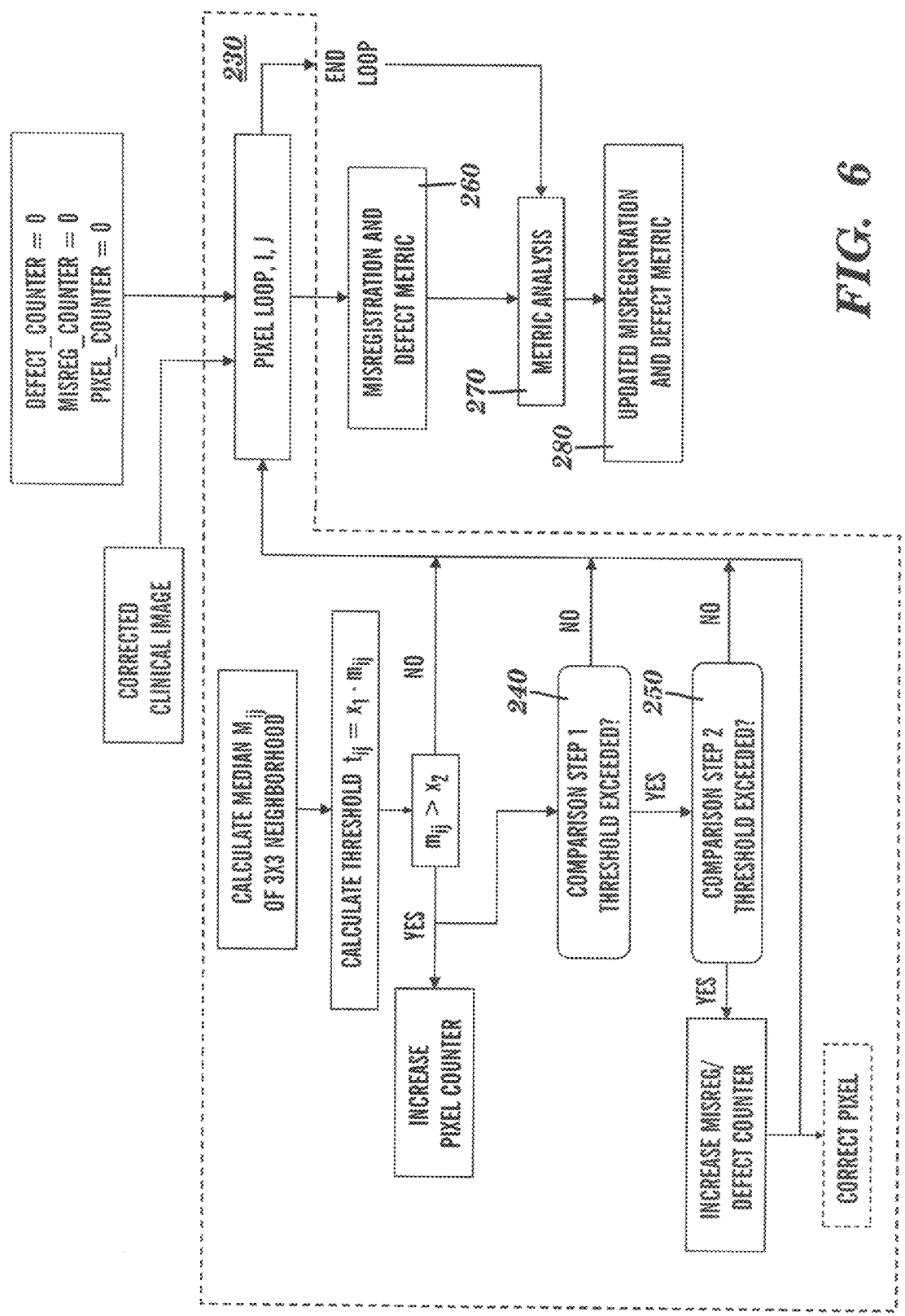
FIG. 6 is a logic flow diagram that shows processing for each pixel according to one embodiment.
Figure 7:
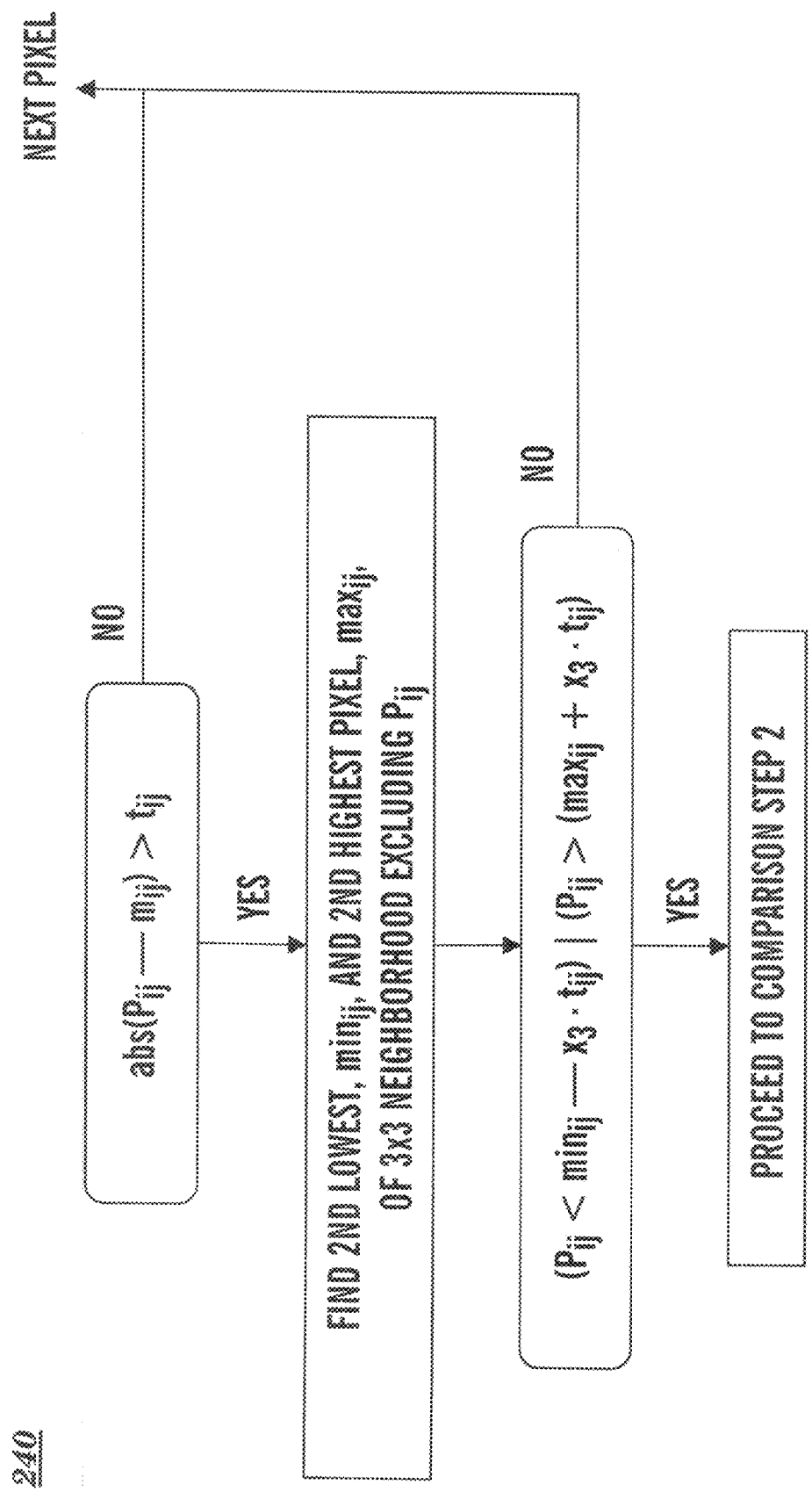
FIG. 7 is a logic flow diagram that expands upon the sequence for a first comparison of image pixels.
Figure 8:
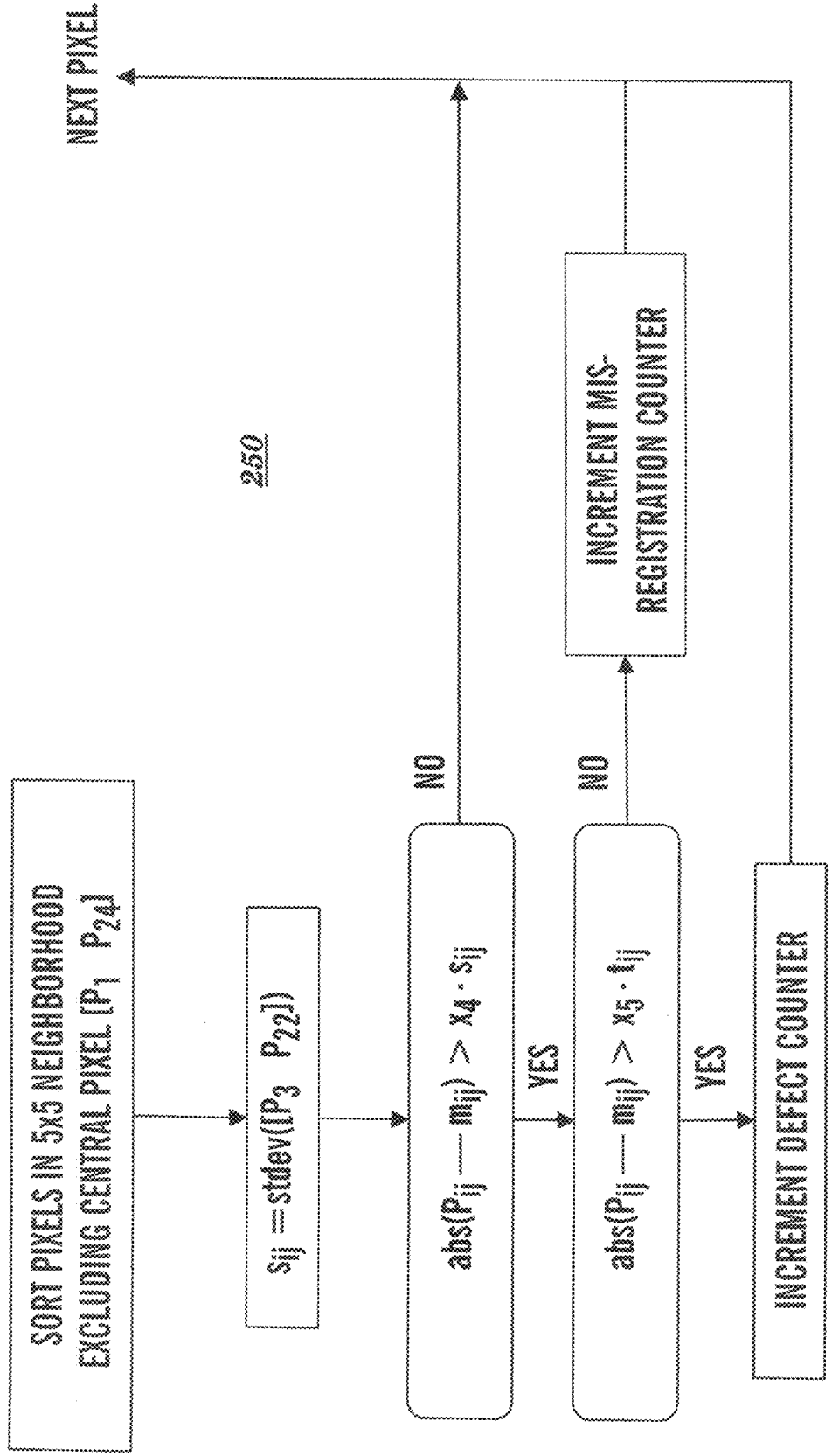
FIG. 8 is a logic flow diagram that expands upon the sequence for a second comparison of image pixels.
Figure 9:
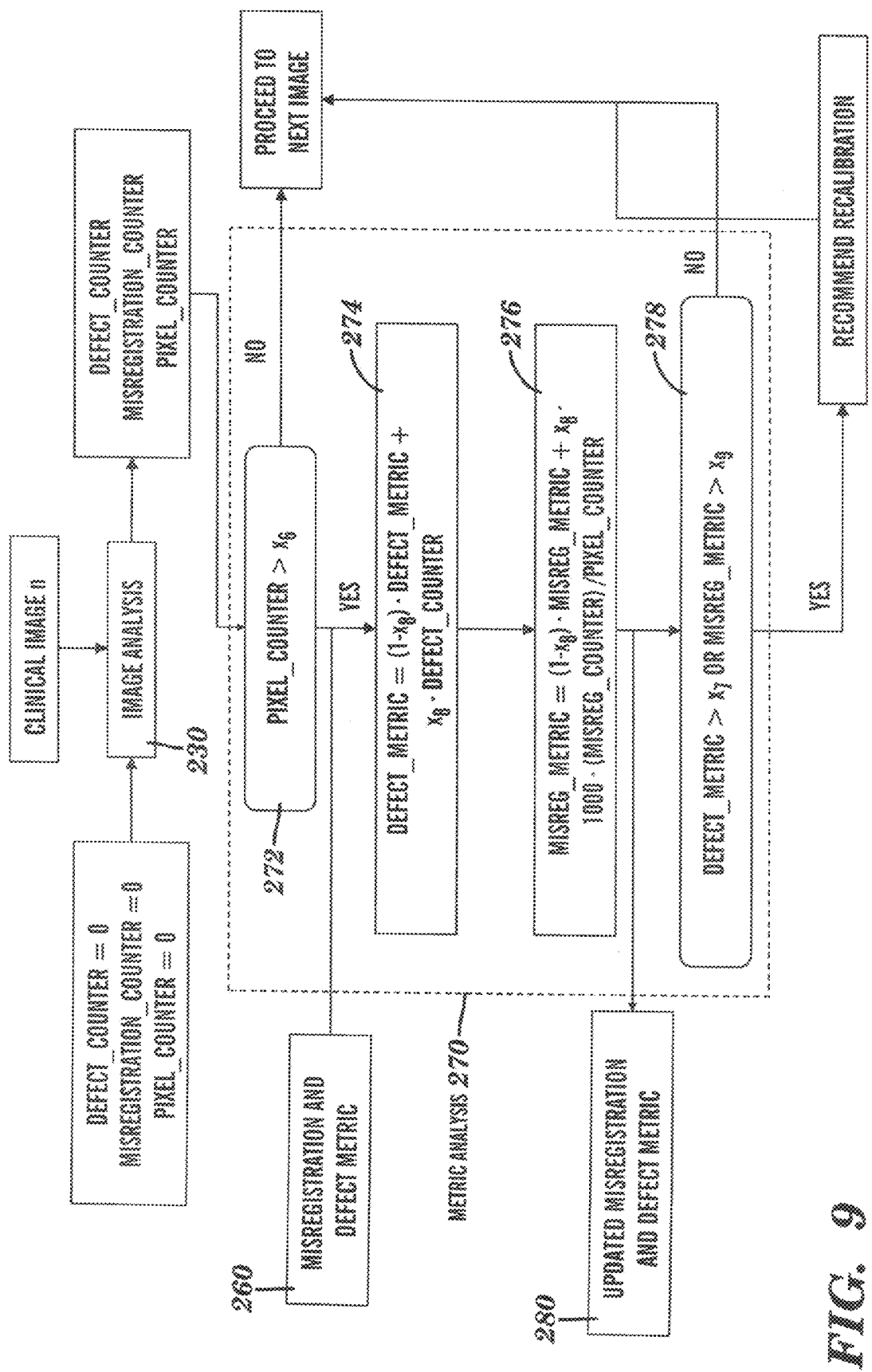
FIG. 9 is a logic flow diagram showing metric analysis for image pixels according to one embodiment.

The processing shown in the overall logic flow diagram of FIG. 6 and supporting logic flow diagrams of FIGS. 7-9 shows how the misregistration and defect metrics are calculated for each image obtained in obtain image step 222 of FIG. 4. This processing begins with the obtained image after the existing calibration data has been applied. The looping operation 230 can either loop over every pixel in the image or it can select sub-regions of the image for analysis. For example, in order to reduce computation time, the algorithm could randomly sample one half of the pixels in the image, or it could select larger contiguous fractions of the image to sample a certain proportion of the pixels. Thus, in looping operation 230, the algorithm initially analyzes the 3×3 pixel neighborhood of each pixel that was selected for the loop, assuming that new detects or any deviations in gain produce pixel values that differ significantly from their small neighborhood surroundings. For faster execution, the looping algorithm moves on to the next pixel if the median value $m_{ij}$ of the pixel neighborhood falls below an empirical threshold value $x_2$. Preferred values for $x_2$ fall between 0.5 and 5 percent of the saturation level of the detector in one embodiment. The thresholding operations make use of the observation that low exposure areas are frequently covered by collimation blades and are masked in subsequent image processing and that at low exposures, any gain misregistration artifacts are masked by electronic noise. Otherwise, the pixel counter is incremented and a threshold code value $t_{ij}$ is computed from the pixel neighborhood based on a derived statistical measure, such as the median value and an empirically determined scalar multiplier $x_1$. Preferred settings for $x_1$ fall between 0.02 and 0.1 in one embodiment.

The analysis continues to a first comparison step 240, which is shown in more detail in FIG. 7. In first comparison step 240, shown in FIG. 7, the pixel value $P_{ij}$ is first compared with the median $m_{ij}$ of the 3×3 pixel neighborhood. If the difference exceeds a threshold, $t_{ij}$, which is preferably proportional to the image code value, the pixels in the 3×3 pixel neighborhood, excluding the central pixel, are sorted in increasing order. This results in 8 sorted pixel values for the 3×3 pixel neighborhood. (That is, excluding the pixel under analysis from the sorted values.)

Further thresholding is now applied using the second lowest $min_{ij}$ and the second highest $max_{ij}$ of the sorted code values. Applicants have noted that using these inner values instead of the extreme minimum and maximum improves the chance of capturing larger clusters of defective or mis-registered pixels. Alternately, the third largest and third smallest pixels could be selected for thresholding to detect even larger clusters, but this tends to capture an excessive number of potentially defective pixels in the presence of strong high-frequency gradients. As such, this can tend to decrease the computational efficiency of the algorithm. The ordering operations described above can be considered two-dimensional order-statistic filters. Median calculation is a special case for using two-dimensional order-statistic filters. As is well known, the median of a finite list of numbers can be lbund by sorting the numbers from lowest value to highest value and picking the middle one. If there is an even number of observations, then there is no single middle value; in such a case the mean of the two middle values is taken as the median.

In the embodiment according to FIG. 7, the analysis proceeds to second comparison step 250 of FIG. 8, if either the central pixel is by a factor $x_3$ times the threshold lower than the second lowest sorted pixel value, $min_{ij}$ or the central pixel is by a factor $x_3$ times the threshold $t_{ij}$ higher than the second highest sorted pixel value, $max_{ij}$. Value $x_3$ is a scalar multiplier, empirically determined; preferred values fall between 0.5 and 2 in one embodiment. These selection criteria ensure that any identified misregistered or defective pixels are lower or higher than the maxima and minima of their local neighborhoods (possibly excluding a small number of other candidate misregistered or defective pixels).

Similar statistical thresholding analysis for defect identification in clinical imaging has been previously proposed, such as in the earlier-cited Maac et al. ∝5934 application. However, Applicants note that this type of thresholding tends to capture an excessive number of potentially defective pixels in some types of images. This may cause difficulties with images that have strong high-frequency gradients because certain types of grids were used, or because jewelry or medical hardware were present, for example. Thresholding of this type can also be misleading where the background is textured because of various items of clothing. Conventional thresholding can also miss larger defective areas. In the embodiment of FIGS. 6-8, first comparison step 240 helps to reduce the number of pixels upon which the more computationally intense processing of second comparison step 250 must be performed.

If the thresholds for comparison step 240 are exceeded as shown in FIG. 7, the second part of the analysis, in second comparison step 250 of FIG. 8 is performed. This second part is based on the larger 5×5 pixel neighborhood and shown in more detail in FIG. 8. In this processing, code values in the 5×5 neighborhood of the pixel, excluding the central pixel, are first sorted in order. The standard deviation $s_{ij}$ of the sorted pixels, or other suitable statistical measure, is calculated, excluding the two lowest and highest code values. If the difference between the pixel value and the median of the 3×3 neighborhood, calculated in comparison step 240, exceeds a pre-determined multiple $x_4$ of the calculated standard deviation, the pixel counter for defective or misregistered pixels is incremented. Otherwise, the algorithm proceeds to the next pixel. Preferred values for the scalar $x_4$ fall between 3 and 10 in one embodiment. Optionally, as shown in FIG. 6, the pixel identified as defective and/or misregistered can be corrected at this point using nearest neighbor interpolation techniques known in the art.

In the embodiment shown in FIG. 8, a pixel is characterized as defective, as opposed to misregistered, if the pixel value $P_{ij}$ deviates from the median $m_{ij}$ of the 3×3 neighborhood by more than a pre-defined threshold determined using a scalar $x_5$ of the initially defined threshold value $t_{ij}$. For example, pixels that deviate by more than 3 to 10× of the threshold, $t_{ij}$, from their surroundings, e.g., the median $m_{ij}$, may be characterized as defects. Those skilled in the art can recognize that other decision criteria could be employed to distinguish misregistered from defective pixels. For example, pixels could be identified as misregistered if they deviate by more than a scalar factor, e.g. 6 times the standard deviation, from the local median $m_{ij}$. A higher threshold could be employed for defects. For example it may be a requirement that defects deviate by more than a second, larger scalar factor, e.g. 10 times the standard deviation, from the local median $m_{ij}$.

Referring again to the sequence of FIG. 6, in a metric analysis step 270, metrics are calculated for each analyzed image based on the count of misregistered and defective pixels. An example of a metric is the ratio of the number of misregistered pixels relative to the number of pixels exceeding the initial threshold code value $x_2$. Thresholds for triggering recalibration can be set based on the metrics calculated for each individual analyzed image, or based on a running average over many images.

As shown in FIG. 6, at step 280, the misregistration and defect metric is updated.

FIG. 9 shows the preferred embodiment of metric analysis step 270 in more detail. Initially, counters for pixel defects and pixel misregistration as well as total pixel count (pixels per image exceeding the threshold $x_2$ in FIG. 6) are reset to zero. Following the image analysis of looping step 230 (FIG. 6), values are provided for each of these counters. A metric analysis step 270 then executes, using these values. In a comparison step 272, the total pixel count is compared against a threshold value $x_6$, which is empirical parameter with preferred settings between 1000 and 100,000. If the total pixel count is below this threshold, no further action is taken and the next image can be processed. Such a threshold improves the robustness of the algorithm because many images contain few defects and misregistered pixels out of many millions of total pixels. If the analysis is based on too few total pixels, a single defective or misregistered pixel in the analyzed sub-region of the detector can skew the result.

If the total pixel count exceeds threshold $x_6$, the module reads in the stored values of the misregistration and defect metrics 260. These values can be stored in an array, keeping track of the history for all or a subset of images captured on the detector. If an array of metric values is read in, in most cases a subset of the stored values, preferably the stored value for the previous image, will be used in the computation of the updated defect and misregistration metrics 270. The pixel defect metric is then computed in a first computation step 274. Multiplier $x_8$ with preferred settings between zero and one is used to compute a weighted average of the previously stored defect metric and the count of defective pixels for the current image. A second computation step 276 performs a similar weighted calculation to obtain the updated misregistration metric. Thus, in one embodiment, the current misregistration and defect metrics are weighted averages of the previously stored misregistration and defect metrics and a mathematical formula including the misregistration and defective pixel counters of captured medical image under analysis. Then, in a comparison step 278, defect and misregistration metrics are compared against empirically determined stored threshold values $x_7$ and $x_9$, respectively. Preferred settings for $x_7$ and $x_9$ are empirically determined and depend on the formula for each metric. If either value exceeds its corresponding threshold, recalibration is recommended.

It is instructive to note that the method of the present invention is performed on clinical image data, following any applied processing and correction algorithms for defective pixels that had previously been identified. That is, any correction algorithms have already been applied to the patient image data as a result of the preceding calibration. Thus, defective and misregistered pixels that are found and processed using these procedures are newly identified defects. Not all of these defects are intended for adding to the defect map for the particular DR detector, however. Defects that have been identified as misregistered can be corrected upon the next calibration. The various thresholds that are used in this processing can be empirically determined or can be functions of a statistical measure.

The invention makes use of the fact that most misregistration artifacts are initially below the visual threshold and that a small number of uncorrected single pixel defects in the images can be tolerated by the user. Thus the images are processed as quickly as possible during normal operation of the detector without delays because of additional image corrections. However, if the thresholds for acceptability and visibility are exceeded the user is reminded to perform a gain calibration.

In summary, an embodiment of the invention is a method for monitoring the state of calibration of a digital x-ray detector, the detector comprising a solid state sensor with a plurality of pixels, a scintillating screen, and at least one embedded microprocessor. The method comprises using a computer or the embedded microprocessor or both during normal diagnostic use of the detector. Initially, the digital image is captured and corrected for gain, offset and defects. Processing then calculates a misregistration metric that is indicative of movement of the sensor panel relative to the scintillating screen. Calculation of the misregistration metric includes steps of:

(i) for each pixel in at least one region of the sensor, determining a median value of all pixels in a small neighborhood of pixels surrounding each identified pixel;

(ii) identifying those pixels for which the median value of the small neighborhood exceeds a first predetermined threshold;

(iii) determining, for each neighborhood of the pixel identified in the previous step, a first difference between the median value and the code value of its respective identified pixel;

(iv) determining whether or not the first difference exceeds a second predetermined threshold and, if the second predetermined threshold is exceeded, sorting the pixels surrounding the identified pixel in increasing order of code value;

(v) if the pixel value is lower than the median value, comparing the difference between the second lowest code value from the increasing order and the pixel value to a third predetermined threshold; if the pixel value is higher than the median value, comparing the difference between pixel value and the second highest code value from the increasing order to a third predetermined threshold;

(vi) if the third predetermined threshold is not exceeded, determining that the identified pixel is acceptable;

(vii) if the third predetermined threshold is exceeded, establishing a larger neighborhood of pixels surrounding the respective identified pixel;

(viii) sorting the pixels surrounding the identified pixel in the larger neighborhood in increasing order of code value;

(ix) determining a standard deviation of the code values of the sorted pixels from the larger neighborhood, excluding one or two of the highest and lowest code values; and, if the first difference exceeds a first predetermined multiple of the standard deviation but falls below a second predetermined multiple of the standard deviation, determining that the identified pixel is misregistered and incrementing a misregistration counter if the pixel is identified as misregistered;

(x) after all pixels of the at least one region have been analyzed, calculating the current misregistration metric based on the incremented misregistration counter; and (xi) storing the current misregistration metric on the computer or the embedded processor or both.

The current misregistration metric is a weighted average of the previously stored misregistration metric and a mathematical formula including the misregistration counter of captured medical image under analysis. The misregistration metric can optionally be displayed to the user.

A second embodiment of the present invention is a method for monitoring the state of calibration of a medical digital x-ray detector, the detector, comprising a solid state sensor with a plurality of pixels, a scintillating screen, and at least one embedded microprocessor. The method comprises using a computer or the embedded microprocessor or both during normal diagnostic use of the detector. Initially, the digital image is captured and corrected for gain, offset and defects. Processing then calculates a defect metric indicative of abnormal properties of pixels in the sensor, including steps of:

(i) for each pixel in at least one region of the sensor, determining a median value of all pixels in a small neighborhood of pixels surrounding each identified pixel;

(ii) identifying those pixels for which the median value of the small neighborhood exceeds a first predetermined threshold;

(iii) determining, for each neighborhood of a pixel identified in the previous step, a first difference between the median value and the code value of its respective identified pixel;

(iv) determining whether the first difference exceeds a second predetermined threshold and if the second predetermined threshold is exceeded, sorting the pixels surrounding the identified pixel in increasing order of code value;

(v) if the pixel value is lower than the median value, comparing the difference between the second lowest code value from the increasing order and the pixel value to a third predetermined threshold;

(vi) if the pixel value is higher than the median value, comparing the difference between pixel value and the second highest code value from the increasing order to a third predetermined threshold;

(vii) if the third predetermined threshold is not exceeded, determining that the identified pixel is acceptable;

(viii) if third predetermined threshold is exceeded, establishing a larger neighborhood of pixels surrounding the respective identified pixel;

(ix) sorting the pixels surrounding the identified pixel in the larger neighborhood in increasing order of code value;

(x) determining a standard deviation of the code values of the sorted pixels from the larger neighborhood, excluding one or two of the highest and lowest code values; and it the first difference exceeds a predetermined multiple of the standard deviation, determining that the identified pixel is defective and incrementing a defect counter if the pixel is identified as defective;

(xi) after all pixels of the at least one region have been analyzed, calculating the current defect mettle based on the incremented defect counter; and (xii) storing the current defect metric on the computer or the embedded processor or both.

The current defect metric is a weighted average of the previously stored defect metric and a mathematical formula including the defect counter of captured medical image under analysis. The defect metric can optionally be displayed to the user.

Figure 10:
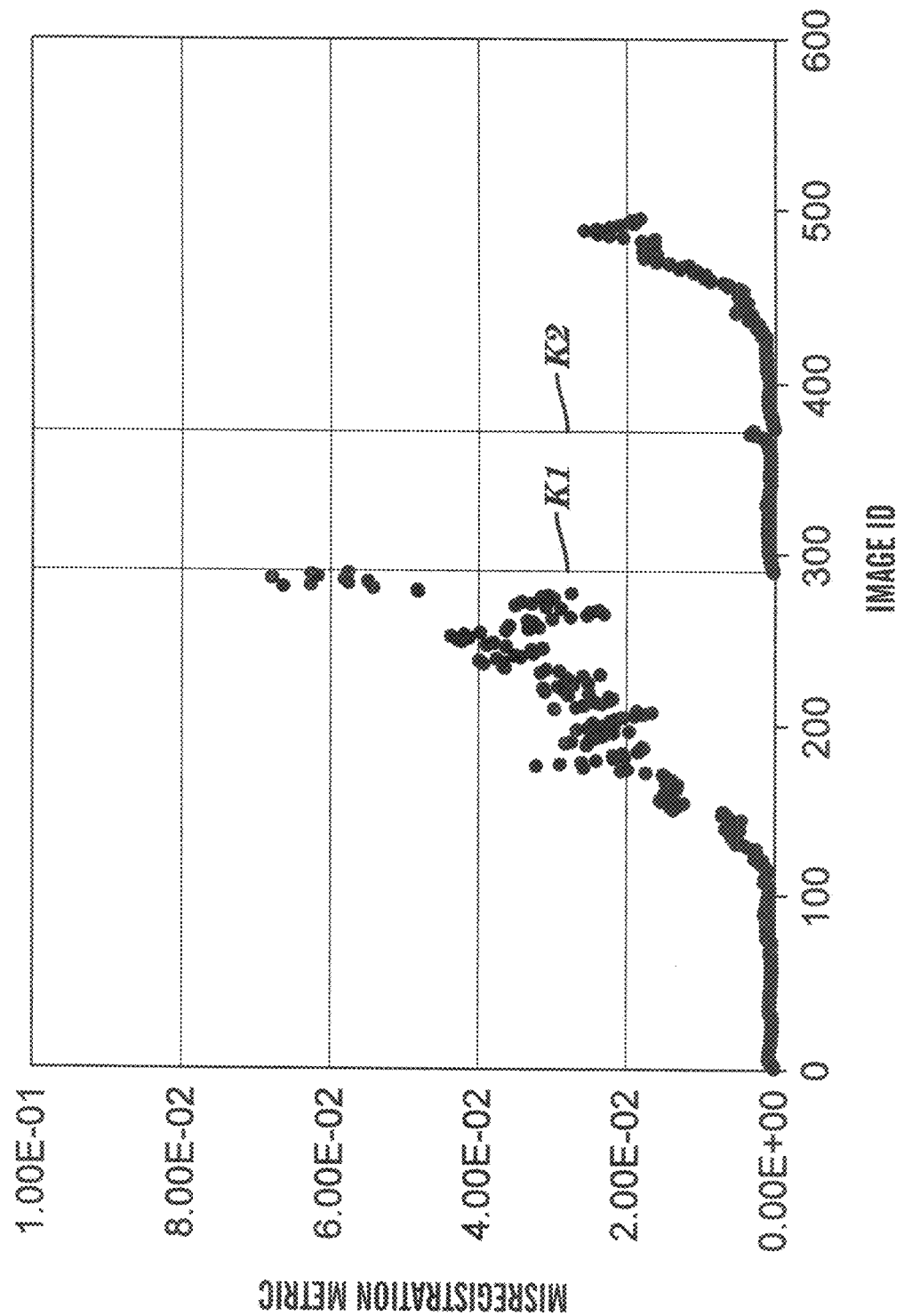
FIG. 10 is a graph showing exemplary behavior for misregistration errors with handling over time and relative to detector calibration.

The graph of FIG. 10 shows misregistration results in one clinical trial for a single DR x-ray detector using the method of the present invention. Use cycles are indicated along the horizontal axis. Repeated handling of the DR detector causes an increasing number of misregistered pixels. Monitoring using the method of the present invention tracks the number of misregistered pixels and computes the misregistration metric as described earlier. This value increases with repeated use and can be accelerated with rough handling. At time or image counts K1 and K2, indicated by vertical lines, recalibrations were performed. The number of misregistered pixels dropped significantly with recalibration, as shown.

Figure 11:
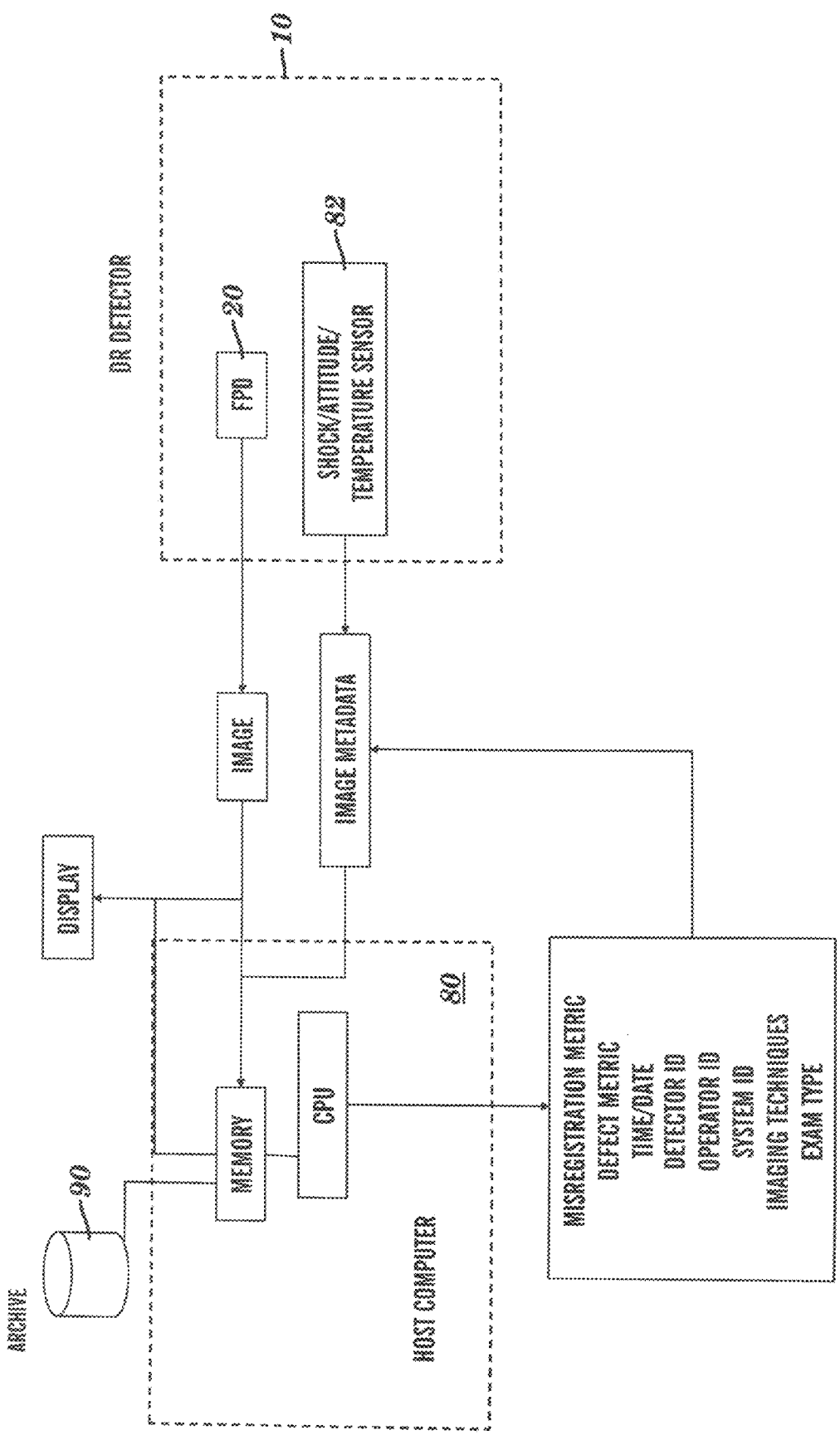
FIG. 11 is a schematic diagram showing how image metadata can be obtained, stored, and used along with image and defect data.

The various thresholds that are used in this processing can be empirically determined or can be functions of a statistical measure. The misregistration and defect metrics can be stored on the on-board control logic processor 70 or on host computer 80, along with various ancillary system data, such as any of a time, system operator, system name, detector serial number, location, temperature, and shock and vibration values, for example, as shown in FIG. 11. These parameters are part of the image metadata that can originate from the detector itself, e.g., temperature and shock data or detector ID/serial number, and other data relating to the operation of the panel, or from the host computer. Many of the image metadata stem from interactions of the user with the host computer, e.g., the detector ID when the detector is first registered on the computer, the name or operator ID, the type of examination to be performed, and the exposure technique for the examination. Image metadata can be stored together with the images in a permanent image archive 90, such as controlled through a networked host, and/or on the host computer itself. The misregistration and defect metrics can be part of the image metadata or they can be stored together with the other ancillary system data in a separate file. In one embodiment, the system is further capable of displaying the misregistration or defect metric, or both, to the system user or administrator as a function of any ancillary system data.

In a clinical setting it may become apparent that some environments or operators cause more frequent calibrations than others because of rougher than normal handing. Because this leads to undesirable system downtime the system administrator could arrange more training for these operators on how to use the detector or can take other steps to reduce rough handling. Historical data about defects and misregistration are also available for the manufacturer or system supplier, helping to track how well different detectors perform over time. Moreover, widely different uses can be expected for different installations because of the portability of the detector, and some sites may require more frequent calibrations than others. Usage statistics such as the misregistration and defect metrics identified using the method and apparatus of the present invention can help the manufacturer to make further improvements to detector design and help to reduce the needed frequency of calibration.

Figure 12:
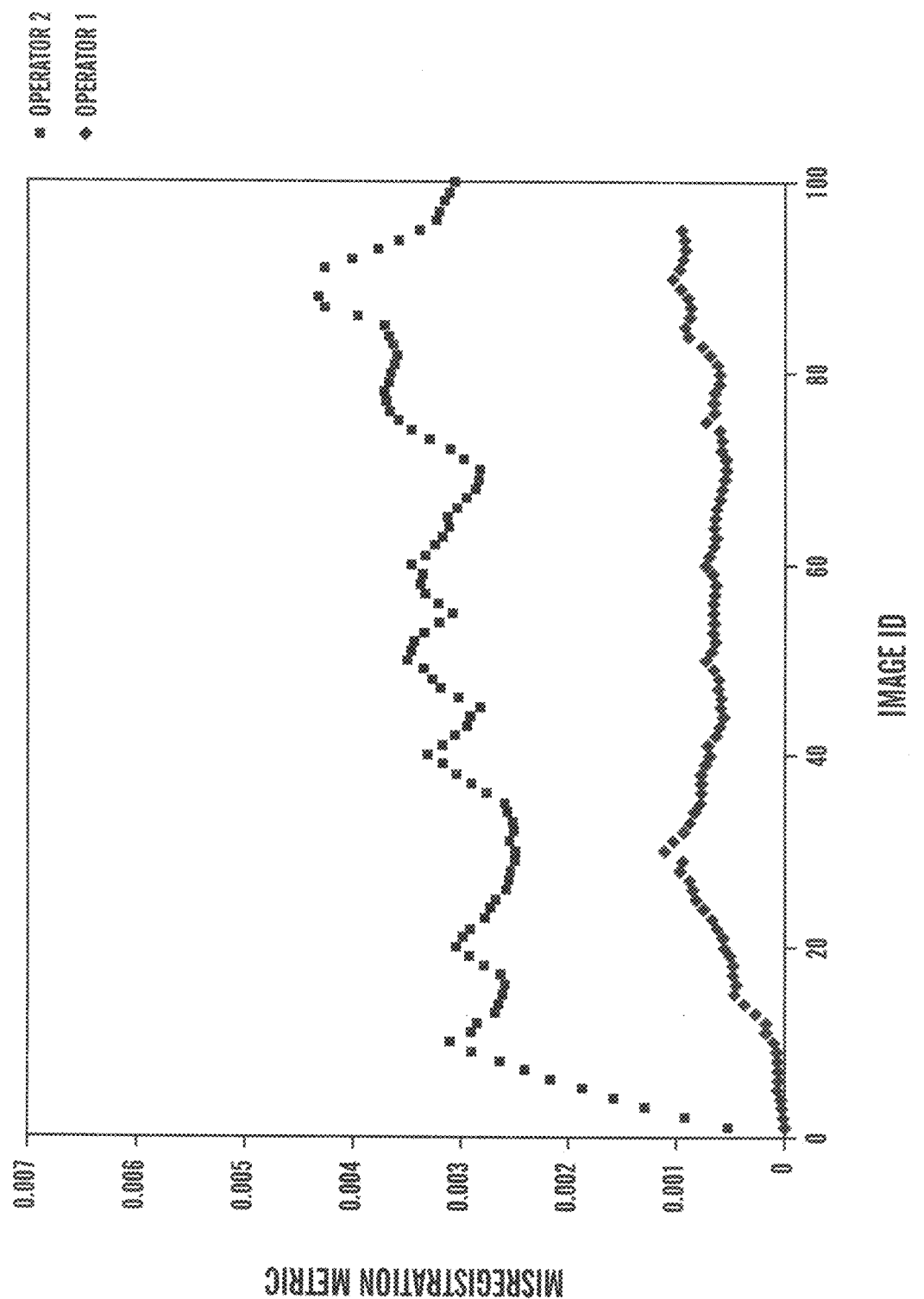
FIG. 12 is an example of a graph showing misregistration data for two different system operators.

FIG. 12 shows an example where the misregistration data is displayed for two different system operators. Operator 1 was instructed to handle the detector normally. Operator 2 was asked to perform some rough handling, for example small bumping and jarring, for example when moving the detector between positions or when inserting it into a bucky. The misregistration metric for the images taken by operator 2 is significantly higher.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10. DR detector
14. Scintillator screen
20. Flat-panel detector
22. Photosensor
24. Pixel
25. Readout elements
26. Switch element
30. Defective pixel
32. Misregistered pixel
60. X-ray source
62. Subject
64. Generator
66. Generator interface
70. Control logic processor
72. Wireless interface
74. Power supply
76. Battery
78. Power regulator
80. External host computer
82. Sensor
84. Wireless interface
86. Control circuitry
88. Image correction and calibration circuitry
90. Archive system
100. Radiographic system
200. Gain calibration procedure
201. Capture step
202. Averaging step
204. Capture step
205. Analysis step
206. Candidate defect map
207. Qualification step
208. Update step
210. Reset step
220. Gain calibration monitoring process
222. Obtain image step
224. Detect metric calculation step
226. Misregistration calculation step
230. Looping operation
240. Comparison step
250. Comparison step
260. Stored misregistration and detect metric
270. Metric analysis step 272, 278. Comparison step
274, 276. Computation step
280. Updated misregistration and defect metric
K1, K2. Time or image count
$m_{ij}$ Median
$P_{ij}$ Pixel value
$s_{ij}$ Standard deviation
$t_{ij}$ Threshold
$x_1, x_3, x_4, x_5, x_8$. Scalar multiplier
$x_2, x_6, x_7, x_9$. Threshold value

What is claimed is:

1. A method for monitoring the state of calibration of a digital x-ray detector, the detector comprising a solid state sensor, a scintillating screen and at least one embedded microprocessor, the solid state sensor comprising a plurality of pixels, the method comprising using a computer or the embedded microprocessor or both, during normal diagnostic use of the detector, to perform steps of:
 accessing a digital image including digital image data;
 calculating a misregistration metric from the digital image data indicative of movement of the solid state sensor relative to the scintillating screen;
 calculating a defect metric from the digital image data indicative of abnormal properties of pixels in the solid state sensor;
 determining whether one or both of the misregistration metric and the defect metric exceeds a respective, preselected threshold value; and
 alerting a user of the detector to conduct a calibration of the solid state sensor when either or both of the respective threshold values has been attained.

2. The method according to claim 1, further comprising a step of correcting portions of the image for any pixel corresponding to the misregistration metric or the defect metric.

3. The method according to claim 1, wherein the detector comprises shock sensors, further comprising steps of:
 monitoring shock events to the detector; and
 correlating monitored shock events to misregistrations and defects.

4. The method according to claim 1, wherein the detector comprises temperature sensors, further comprising steps of:
 monitoring temperature events affecting the detector; and
 correlating temperature events to misregistrations and defects.

5. The method according to claim 1, wherein the calculating steps further comprise:
 correcting the image for gain, offset and defect;
 for each pixel in at least one region of the sensor, defining a small pixel neighborhood surrounding each pixel under analysis;
 deriving at least one first statistical measure from all or a subset of pixels in the small pixel neighborhood;
 comparing each pixel under analysis with the at least one first statistical measure;
 if the result of the first comparing exceeds at least one first predetermined threshold value, defining a larger pixel neighborhood surrounding the pixel under analysis;
 deriving at least one second statistical measure from all or a subset of pixels in the larger pixel neighborhood;
 comparing each pixel under analysis with the at least one second statistical measure;
 determining whether the at least one second statistical measure exceeds a second predetermined threshold;
 if the second predetermined threshold is exceeded, identifying the pixel under analysis as defective or misregistered;
 incrementing a misregistration counter if the difference between the pixel under analysis and the at least one first statistical measure or the at least one second statistical measure falls below a third predetermined threshold;
 incrementing a defective pixel counter if the difference between the pixel under analysis and the at least one first statistical measure or the at least one second statistical measure exceeds the third predetermined threshold;
 after all pixels of the at least one region have been analyzed, calculating current misregistration and defect metrics based on previously stored misregistration and defect metrics and the incremented misregistration and defective pixel counters; and
 storing the current misregistration and defect metrics on the computer or the processor or both.

6. The method according to claim 5, wherein each pixel or a statistical measure of the first pixel neighborhood in the at least one region is compared to a threshold code value and only pixels exceeding the code value are analyzed.

7. The method according to claim 5, wherein deriving the at least one first statistical measure comprises sorting all or a subset of the pixel values in the small pixel neighborhood.

8. The method according to claim 5, wherein a first statistical measure comprises one or more two-dimensional order-statistic filters.

9. The method according to claim 5, wherein a second statistical measure comprises the standard deviation of a subset of sorted pixels of the larger pixel neighborhood.

10. A method for monitoring the state of calibration of a digital x-ray detector, the detector comprising a solid state sensor, a scintillating screen and at least one embedded microprocessor, the solid state sensor comprising a plurality of pixels, the method comprising using a computer or the embedded microprocessor or both, during use of the detector, to perform:
 accessing a digital image including digital image data;
 calculating a misregistration metric from the digital image data indicative of movement of a portion of the plurality of pixels relative to the scintillating screen;
 calculating a defect metric from the digital image data indicative of abnormal properties of pixels in the solid state sensor;
 storing the misregistration and defect metrics together with ancillary system data on a processor or a computer or both; and
 performing an analysis of the misregistration or defect metrics, or both, as a function of at least one of the ancillary system data.

11. The method according to claim 10, wherein the ancillary system data comprises a time, a system operator, a location, a shock or vibration value, a number of images, and a temperature.

12. A system for monitoring the state of calibration of a digital x-ray detector, the detector comprising a solid state sensor, a scintillating screen and at least one embedded microprocessor, the system comprising:
 a computer operable during normal diagnostic use of the detector to access a digital image including digital image data;
 processing means for performing pixelwise computations on the image and calculating a misregistration metric indicative of movement of the solid state sensor relative to the scintillating screen;
 processing means for calculating a defect metric indicative of abnormal properties of pixels in the solid state sensor;

processing means for determining whether one or both of the misregistration metric and the defect metric exceeds a respective threshold value; and means for alerting a user of the system to conduct a calibration of the detector when either one or both of the respective threshold values have been exceeded.

13. The system according to claim 12, wherein the detector is portable, comprising a battery and supporting a wireless link to the computer, where the misregistration metric operates to identify temporary changes in pixel sensitivity correctable by re-calibration.

14. The system according to claim 12, wherein the detector comprises at least one shock sensor for monitoring mechanical shock to the detector, and the system further comprises means for alerting a system user to conduct a calibration of the detector when a preselected shock threshold value has been exceeded.

15. The system according to claim 12, wherein the detector comprises at least one temperature sensor, and the system further comprises means for alerting a system user to conduct a calibration of the detector when a preselected upper or lower temperature threshold value has been exceeded.

16. The system according to claim 12, wherein the means for performing pixelwise computations further comprises means for correcting the identified misregistered or defective pixels, or both.

17. The system according to claim 12, further comprising:
means for conducting a calibration step;
means to identify any pixels with abnormal properties that are not marked as defective in the current defect map of the detector; and
means for updating the current defect map with the newly identified pixels.

18. A system for monitoring the state of calibration of a digital x-ray detector, the detector comprising a solid state sensor with a plurality of pixels, a scintillating screen and at least one first computer processor, the system comprising:
a first device configured to access a digital image comprising digital image data;
a second computer processor operable during normal diagnostic use of the detector, in cooperation with the at least one first computer processor configured to;
perform pixelwise computations on the image and calculate a misregistration metric indicative of movement of the solid state sensor relative to the scintillating screen;
calculate a defect metric indicative of abnormal properties of pixels in the solid state sensor;
where the misregistration and defect metrics are stored together with ancillary system data on the at least one first computer processor or the second computer processor or both;
where the misregistration metric or the defect metric, or both, are displayed as a function of any ancillary system data to the system user.

19. The system according to claim 18, where the second computer processor in cooperation with the at least one first computer processor are configured to analyze the misregistration metric or defect metric, or both, as a function of at least one of the ancillary system data, where the ancillary data is any of a time, system operator, location, temperature, shock and vibration.

20. A method for monitoring the state of calibration of a digital x-ray detector, the detector comprising a solid state sensor, a scintillating screen and at least one embedded microprocessor, the solid state sensor comprising a plurality of pixels, the method comprising using a computer or the embedded microprocessor or both, during use of the detector, the method comprising:
accessing a digital image including digital image data;
calculating a misregistration metric from the digital image data indicative of movement of the solid state sensor relative to the scintillating screen;
storing the misregistration metric at one of the detector and the computer or displaying the misregistration metric.

21. The method of claim 20, comprising:
calculating a defect metric from the digital image data indicative of abnormal properties of pixels in the solid state sensor;
determining whether one or both of the misregistration metric and the defect metric exceeds a respective, preselected threshold value, where the misregistration metric is indicative of temporary changes in pixel sensitivity correctable by re-calibration; and
alerting a user of the detector to conduct a calibration of the solid state sensor when either or both of the respective threshold values has been attained.

* * * * *

UNITED STATES PATENT AND TRADEMARK OFFICE
CERTIFICATE OF CORRECTION

PATENT NO.        : 8,519,348 B2                                            Page 1 of 1
APPLICATION NO.   : 12/643276
DATED             : August 27, 2013
INVENTOR(S)       : Karin Topfer et al.

It is certified that error appears in the above-identified patent and that said Letters Patent is hereby corrected as shown below:

In the Specification

| | |
|---|---|
| Column 2, line 49 | Please replace the word "on-hoard" with the word --on-board-- |
| Column 5, Line 28 | Please replace the word "portable." with the word --portable-- |
| Column 9, Line 1 | Please replace the words "value and" with the words --value $m_{ij}$ and-- |
| Column 9, Line 48 | Please replace the word "α5934" with the word --'5934- -- |
| Column 13, Line 9 | Please replace the word "mettle" with the word --metric-- |

Signed and Sealed this
Twenty-second Day of April, 2014

Michelle K. Lee
*Deputy Director of the United States Patent and Trademark Office*